United States Patent [19]

Wu

[11] Patent Number: 5,245,103
[45] Date of Patent: Sep. 14, 1993

[54] ISOMERIZATION PROCESSES AND CATALYSTS THEREFOR

[75] Inventor: An-hsiang Wu, Bartlesville, Okla.

[73] Assignee: Phillips Petroleum Company, Bartlesville, Okla.

[21] Appl. No.: 963,166

[22] Filed: Oct. 19, 1992

[51] Int. Cl.$^5$ .............................................. C07C 5/13
[52] U.S. Cl. ..................... 585/743; 585/734; 585/741; 585/744; 585/747; 585/748
[58] Field of Search ............... 583/734, 741, 743, 744, 583/747, 748

[56] References Cited

U.S. PATENT DOCUMENTS

| | | | |
|---|---|---|---|
| 2,917,565 | 12/1959 | Carr | 585/734 |
| 3,032,599 | 5/1962 | Holm et al. | |
| 3,238,272 | 3/1966 | Nixon | |
| 3,248,343 | 4/1966 | Kelly et al. | |
| 3,766,286 | 10/1973 | Olah | |
| 3,925,495 | 12/1975 | Rodewald | |
| 3,976,714 | 8/1976 | Rodewald | |
| 3,984,352 | 10/1976 | Rodewald | |
| 4,100,213 | 7/1978 | Rodewald | |
| 4,123,379 | 10/1978 | Gates et al. | |
| 4,201,730 | 5/1980 | Olah | 585/730 |
| 4,424,387 | 1/1984 | Kramer | 585/743 |
| 4,719,190 | 1/1988 | Drago et al. | 585/744 |

OTHER PUBLICATIONS

"Reactions of Butane and Isobutane Catalyzed by Titanium Dioxide Treated with Sulphate Ion . . . ", by M. Hino et al., J. Chem. Soc. Comm. 1979, pp. 1148-1149.
"Reactions of Butane and Isobutane Catalyzed by Zirconium Oxide Treated with Sulfate Ion . . . ", by M. Hino et al., J. Amer. Chem. Soc. 101:21, Oct. 10, 1979, pp. 6439-6441.
"Synthesis of Solid Superacid Catalyst . . . ", by M. Hino et al., J. Chem. Soc. Comm. 1980, pp. 851-852.
"Reaction of Butane to Isobutane Catalyzed by Iron Oxide Treated with Sulfate Ion . . . ", by M. Hino et al., Chemistry Letters, 1979, pp. 1259-1260.
"Superacids", by G. Olah et al., John Wiley and Sons, 1985, pp. 53-61.

Primary Examiner—Patrick P. Garvin
Assistant Examiner—E. D. Irzinski
Attorney, Agent, or Firm—K. K. Brandes

[57] ABSTRACT

In one embodiment, $C_4$-$C_{10}$ alkanes and/or $C_5$-$C_{10}$ cycloalkanes are isomerized in the presence of a catalyst which has been prepared by heating $AlCl_3$, at least one aluminum sulfate-containing support material and at least one chlorinated hydrocarbon (preferably $CCl_4$) at about 40°–90° C., followed by separating the formed solid from the chlorinated hydrocarbon.

In another embodiment, $C_5$-$C_{10}$ cycloalkane(s) are isomerized in the presence of a catalyst which has been prepared by heating $AlCl_3$, at least one sulfur-containing acid ($H_2SO_4$ and/or $ClSO_3H$ and/or $FSO_3H$ and/or $CF_3SO_3H$) and at least one chlorinated hydrocarbon (preferably $CCl_4$) at about 40°–90° C., followed by separating the formed solid from the chlorinated hydrocarbon.

20 Claims, No Drawings

ISOMERIZATION PROCESSES AND CATALYSTS THEREFOR

BACKGROUND OF THE INVENTION

This invention relates to the isomerization of alkanes and/or cycloalkanes.

The use of supported aluminum chloride catalysts for alkane isomerization is known. The present invention is directed to the use of novel, effective $AlCl_3$-containing catalyst materials for alkane and/or cycloalkane isomerization.

SUMMARY OF THE INVENTION

It is an object of this invention to employ materials prepared from aluminum chloride and various sulfur containing compounds as catalysts for isomerizing alkanes and/or cycloalkanes. Other objects and advantages will be apparent from the detailed description of the invention and the appended claims.

In one embodiment of this invention, a process for isomerizing saturated hydrocarbons comprises contacting, at a reaction temperature of about 0°-100° C. (preferably about 20°-50° C.), at least one saturated hydrocarbon selected from the group consisting of alkanes containing 4-10 carbon atoms per molecule and cycloalkanes containing 5-10 carbon atoms per molecule with a solid catalyst composition at effective isomerization conditions;

wherein said catalyst composition has been prepared by a method comprising the steps of (I) heating in the substantial absence of water, at a temperature of about 40°-90° C., a mixture comprising (a) aluminum chloride, (b) at least one chlorinated hydrocarbon having a normal boiling point (i.e., the boiling point at 1 atm. pressure) of about 40°-90° C., and (c) at least one solid aluminum sulfate-containing support material having been prepared by a method which comprises (1) combining an aqueous solution of at least one aluminum salt (preferably Al nitrate) with an aqueous solution of ammonium sulfate such as to provide a $SO_4$:Al molar ratio (equivalent to a S:Al atomic ratio) of about 0.1:1 to about 1:1 in the obtained combined solution, (2) adding at least one base (preferably ammonium hydroxide) to the combined aqueous solution of the aluminum salt and ammonium sulfate obtained in step (1) at such conditions as to form a precipitate, (3) separating the precipitate formed in step (2) from the combined aqueous solution, and (4) calcining the separated precipitate formed in step (3) at about 500°-700° C. for at least about 1 hour; and (II) separating the solid material contained in the reaction mixture obtained in step (I) from said at least one chlorinated hydrocarbon under a dry gas atmosphere.

In another embodiment of this invention, a process for isomerizing saturated hydrocarbons comprises contacting, at a reaction temperature of about 0°-100° C. (preferably about 20°-50° C.), at least one saturated hydrocarbon selected from the group consisting of cycloalkanes containing 5-10 carbon atoms per molecule with a solid catalyst composition at effective isomerization conditions;

wherein said solid catalyst composition has been prepared by a method comprising the steps of (A) heating in the substantial absence of water, at a temperature of about 40°-90° C., a mixture comprising (i) aluminum chloride, (ii) at least one sulfur-containing acid selected from the group consisting of sulfuric acid, chlorosulfonic acid, fluorosulfonic acid and trifluoromethanesulfonic acid, (iii) at least one inorganic support having a $BET/N_2$ surface area of at least about 50 $m^2/g$, selected from the group consisting of alumina, silica and silica-alumina, and (iv) at least one chlorinated hydrocarbon (preferably $CCl_4$) having a normal boiling point of about 40°-90° C., wherein the molar ratio of acid agent (ii) to $AlCl_3$ agent (i) is in the range of about 0.1:1 to about 1:1 (preferably about 0.2:1 to about 1:1); and (B) separating the solid material contained in the reaction mixture obtained in step (A) from said at least one chlorinated hydrocarbon under a dry gas atmosphere.

DETAILED DESCRIPTION OF THE INVENTION

Preparation step (I) or, alternatively, preparation step (A) can be carried out in any suitable manner. Generally, substantially dry agents (a), (b) and (c) or, alternatively, substantially dry agents (i), (ii), (iii) and (iv), which are all defined above, are thoroughly mixed under a dry gas atmosphere (preferably a dry inert gas atmosphere, e.g., $N_2$, He, Ar and the like), and the obtained mixture is then heated under a dry inett gas atmosphere at a temperature of about 40°-90° C., preferably about 70°-80° C., for a time period of about 4 to about 120 hours, preferably about 10-30 hours. It is preferred to carry step (I) or, alternatively, step (A) with agitation, either mechanically (e.g., by means of a stirrer) or ultrasonically.

Agent (b) used in step (I) of the first preparation method or agent (iv) used in step (A) of the second preparation method is a chlorinated hydrocarbon or a mixture of two or more chlorinated hydrocarbons having a normal boiling point in the range of about 40°-90° C., preferably about 70°-80° C. Non-limiting examples of suitable chlorinated hydrocarbons are dichloromethane, chloroform (trichloromethane), carbon tetrachloride, 1,1-dichloroethane, 1,2-dichloroethane, 1,1,1-trichloroethane, 1,1-dichloropropane, 2,2-dichloropropane, 1-chlorobutane, 2-chloro-2-methylbutane, and mixtures thereof. The preferred chlorinated hydrocarbon is carbon tetrachloride. Generally the ratio of the weight of the chlorinated hydrocarbon(s) to the combined weight of all the other agents employed in step (I) or, alternatively, in step (A) is about 4:1 to about 20:1.

In the first catalyst preparation method of this invention, the aluminum-sulfate containing support material (c) has been prepared as follows: a solution of at least one water-soluble Al salt (such as Al sulfate, $NH_4Al$ sulfate, Al nitrate and the like; preferably aluminum nitrate) is mixed with an aqueous solution of $(NH_4)_2SO_4$, so as to provide a molar ratio of $SO_4$:Al in the combined aqueous solution of about 0.1:1 to about 1:1, preferably 0.25:1 to about 0.5:1. Generally, the concentration in the Al salt solution is about 0.1 to about 5 mol/l, and the concentration of the $(NH_4)_2SO_4$ solution is about 0.1 to about 5 mol/l. Then enough of an aqueous alkaline solution (i.e., a solution of NaOH or KOH or $NH_3$ in water, preferably $NH_3$ in water which forms $NH_4OH$) is added to the above-described combined aqueous solution until the pH in the combined solution has risen to a pH of at least about 8, preferably about 9-12. Generally, the concentration of the alkaline solution is about 1-25 mol/l base. When enough of the alkaline solution has been added, generally with agitation, to attain a pH of at least about 8, a precipitate forms. The precipitate is believed to be an intimate mixture containing hydrated alumina (or aluminum hydroxide), aluminum hydroxy sulfates such as Al(OH)SO$_4$, Al$_2$(OH)$_4$SO$_4$ and Al$_2$(SO$_4$)$_3$. The precipitate is separated from the combined aqueous solution by any suitable means (preferably by filtration), preferably washed with distilled or deionized water, and then heated for at least about 1 hour (preferably about 2-8 hours), generally at a temperature of about 500°-700° C. (preferably at about 600°-650° C.), either in air or in an inert gas atmosphere (such as N$_2$ or He or Ar). The thus-obtained calcined aluminum sulfate-containing material is then used as agent (c) in step (1) of the first catalyst preparation method of this invention, generally at a weight ratio of AlCl$_3$ to the aluminum sulfate-containing support material, i.e., agent (a) to agent (c), of about 0.2:1 to about 1:1 (preferably about 0.6:1 to about 0.8:1).

In the second catalyst preparation method of this invention, (i) AlCl$_3$ is mixed with (ii) at least one of the above-described S-containing acids (i.e., one acid or two or more than two acids), (iii) at least one of the above-recited inorganic support materials, i.e., dry alumina, dry silica or dry silica-alumina (the latter having generally been prepared by coprecipitating hydrated silica and hydrated alumina followed by drying and calcining) having a surface (determined by the BET method of Brunauer, Emmett and Teller employing N$_2$ gas) of at least about 50 m$^2$/g, preferably about 100-400 m$^2$/g, and (d) at least one chlorinated hydrocarbon (described above). Generally, the molar ratio of to the S-containing acid(s) to AlCl$_3$ is about 0.1:1 to about 1:1 (preferably about 0.19:1 to about 0.75:1), and the weight ratio of AlCl$_3$ to the inorganic support material(s) is about 0.2:1 to about 2:1 (preferably about 0.6:1 to about 0.8:1).

Separation step (II) or, alternatively, separation step (B) can be carried out in any suitable manner. Preferably, the finished reaction mixture obtained in step (I) or, alternatively, step (A) is filtered, and the solid filter cake is substantially dried at any suitable conditions, preferably at subatmospheric (i.e., vacuum) conditions, at a temperature of about 25°-60° C. Preferably, step (II) or, alternatively, step (B) is carried out under a dry inert gas atmosphere (N$_2$, He, Ar, and the like). The finished/dried catalyst particles should be stored under a dry inert gas atmosphere.

Also in accordance with this invention, the catalyst composition prepared by either the first or the second preparation method of this invention (both described above) is employed as a catalyst for isomerizing C$_5$-C$_{10}$ cycloalkanes, preferably methyl-substituted cycloalkanes. Nonlimiting examples of suitable feed cycloalkanes are methylcyclobutane, methylcyclopentane, 1,1-dimethylcyclopentane, 1,2-dimethylcyclopentane, 1,3-dimethylcyclopentane, methylcyclohexane, 1,1-dimethylcyclohexane, 1,2-dimethylcyclohexane, 1,3-dimethylcyclohexane, ethylcyclohexane, methylcycloheptane, 1, methyl-2-ethylcyclopentane, 1,1-dimethylcycloheptane, 1,2-dimethylcycloheptane, 1,3-dimethylcycloheptane, ethylcycloheptane, 1-methyl-2-ethylcyclohexane, methylcyclooctane, 1,1-dimethylcyclooctane, 1,2-dimethylcyclooctane, 1,3-dimethylcyclooctane, and mixtures thereof. The preferred cycloalkane is methylcyclopentane which is substantially isomerized to cyclohexane in accordance with the process of this invention.

Further in accordance with this invention, the catalyst composition prepared by the first preparation method (described above) is employed for partially isomerizing (and partially disproportionating) normal (straight-chain) alkanes and isoalkanes (i.e., branched) alkanes containing 4-10 carbon atoms per molecule. Non-limiting examples of suitable alkanes are n-butane, isobutane, n-pentane, isopentane (i.e., 2-methylbutane), n-hexane, isohexanes (such as 2-methylpentane, 3-methyl-pentane, 2,2-dimethylbutane), n-heptane, isoheptanes (in particular methyl-substituted hexanes and dimethyl-substituted pentanes), n-octane, isooctanes (in particular methyl-substituted heptanes and dimethyl-substituted hexanes), n-nonane, isononanes (in particular methyl-substituted octanes, dimethyl-substituted octanes, trimethyl-substituted heptanes, tetramethyl-substituted hexanes). Presently preferred are C$_4$-C$_8$ n-alkanes and C$_4$-C$_8$ isoalkanes, such as those present in commercial alkylation products (i.e., products obtained by the reaction of an isoalkane such as isobutane with an alkene such as butene-2). Particularly preferred feed alkanes are n-pentane, n-hexane, isopentane (2-methylbutane), n-hexane and 2,2,4-trimethylpentane.

The process for isomerizing C$_4$-C$_{10}$ alkanes and/or C$_5$-C$_{10}$ cycloalkanes with at least one of the above-described catalyst compositions can be carried out under any suitable reaction conditions at a relatively low temperature of up to about 100° C., more preferably about 20°-50° C. (most preferably about 30°-40° C.), generally at about 1-5 atm. pressure, for about 0.1-8 hours. The feed hydrocarbon(s) can be contacted with the catalyst composition in any suitable mode, such as in a slurry-type operation in which the catalyst is dispersed in the feed hydrocarbon(s), or in a fixed catalyst bed operation in which the hydrocarbon feed flows upward or downward through a solid catalyst layer (or several catalyst layers). The time of contact between the feed hydrocarbon(s) and the catalyst composition generally is in the range of about 5 minutes to about 8 hours, preferably about 1-2 hours. Each isomerization process can be carried out as a batch operation or as a continuous operation. Moisture is to be substantially absent during the isomerization process.

The isomerization processes of this invention frequently generate a multitude of products, especially in the case of alkane feeds which do not only partially isomerize but also, to a lesser or greater extent, disproportionate to higher and lower alkanes. Thus, it is generally necessary to separate the various formed hydrocarbons from one another and from unconverted feed hydrocarbons. This separation can be carried out in any suitable manner, generally by fractional distillation (possibly in the presence of an extractant, i.e., by extractive distillation) as is easily determined by persons skilled in the various liquid-liquid separation technologies.

The following examples are presented to further illustrate this invention and are not to be construed as unduly limiting the scope of the invention.

EXAMPLE I

This example illustrates the preparation of aluminum sulfate-containing catalysts for alkane and/or cycloalkane isomerization.

Aluminum sulfate-containing support materials, which were subsequently used in the preparation of isomerization catalysts, were prepared as follows. Six aqueous solutions containing various amounts of aluminum nitrate nonahydrate and ammonium sulfate were prepared as shown below:

| Solution | Amount of Al(NO₃)₃·9H₂O | Amount of (NH₄)₂SO₄ | Vol. of H₂O | Atomic S:Al Ratio* |
|---|---|---|---|---|
| 1 | 75 g (0.2 mol) | 2.64 g | 300 | 0.1:1 |
| 2 | 75 g | 6.61 g | 300 | 0.25:1 |
| 3 | 150 g (0.4 mol) | 26.4 g | 600 | 0.5:1 |
| 4 | 75 g | 26.43 g | 500 | 1:1 |
| 5 | 75 g | 39.64 g | 700 | 1.5:1 |
| 6 (Control) | 75 g | 0.00 | 500 | 0 |

*equivalent to SO₄:Al molar ratio

These aqueous solutions were then mixed with 100 mL of 28 weight-% aqueous ammonia solution so as to form suspended precipitates (believed to be intimate mixtures of aluminum sulfate and hydrated alumina). After about 1-2 hours, the suspensions were filtered. The filter cakes were washed several times with 100 mL aliquots of deionized water, dried for 18-24 hours at 75°-100° C. under vacuum conditions (0.1 torr), and calcined in air for 2-3 hours at 600° C.

The calcined filter cakes which were obtained by the above-described procedure from solutions 1, 2, 3, 4 and 5, respectively, were labeled "Al-S-O Material 1", "Al-S-O Material 2", "Al-S-O Material 3", "Al-S-O Material 4" and "Al-S-O Material 5", respectively. The calcined material obtained from Solution 6 which did not contain (NH₄)₂SO₄ was labeled "Alumina (Control)".

5.0 grams of each of the above-described support materials were mixed with 3.56 grams of anhydrous AlCl₃ and dry, freshly distilled CCl₄. The mixtures were heated, with stirring, for 1.5-3 days under reflux conditions in the dark, under a dry nitrogen atmosphere. The reaction mixtures were dried by evaporating the solvent at room temperature under vacuum conditions (0.1 torr) so as to obtain Catalyst Compositions 1-6.

EXAMPLE II

The catalysts described in Example I were employed in the isomerization of several alkanes (n-pentane, isopentane, n-hexane) and of one cycloalkane (methylcyclopentane). All reactions were carried out at about 33°-38° C. in sealed ampules under a dry nitrogen atmosphere, employing about 10 mL of the feed hydrocarbon (alkane or cycloalkane) and about 0.5 grams of each of the catalysts. The reaction mixtures were slightly agitated for about 1-2 hours by means of an ultrasonic vibrator, and were analyzed by means of a gas chromatograph after reaction times of 1 and 2 hours. Test results are summarized in Tables I-IV.

TABLE I

| | | (Feed: n-Pentane) | | | | |
|---|---|---|---|---|---|---|
| | Reaction | Liquid Product Composition (Weight-%) | | | | % Conversion |
| Catalyst Preparation Method | Time (Hours) | n-Pentane | Isopentane | C₄⁻ Alkanes | C₆⁺ Alkanes | of n-Pentane |
| AlCl₃ + Alumina (Control)[1] | 1 | 94.7 | 3.2 | 1.0 | 1.0 | 5.3 |
| AlCl₃ + Al—S—O Material 1[2] | 1 | 88.8 | 9.0 | 1.1 | 1.1 | 11.2 |
| AlCl₃ + Al—S—O Material 2[3] | 1 | 63.3 | 25.4 | 5.3 | 5.9 | 36.7 |
| AlCl₃ + Al—S—O Material 3[4] | 1 | 56.7 | 31.5 | 3.7 | 8.1 | 43.3 |
| AlCl₃ + Al—S—O Material 4[5] | 1 | 89.5 | 7.8 | 1.2 | 1.5 | 10.5 |
| AlCl₃ + Al—S—O Material 5[6] | 1 | 94.3 | 3.5 | 1.0 | 1.2 | 5.6 |
| AlCl₃ + Alumina (Control)[1] | 2 | 93.4 | 4.3 | 1.3 | 1.0 | 6.6 |
| AlCl₃ + Al—S—O Material 1[2] | 2 | 83.5 | 12.0 | 2.1 | 2.4 | 16.5 |
| AlCl₃ + Al—S—O Material 2[3] | 2 | 56.0 | 28.0 | 7.2 | 8.9 | 44.0 |
| AlCl₃ + Al—S—O Material 3[4] | 2 | 45.1 | 30.9 | 5.6 | 18.5 | 54.9 |
| AlCl₃ + Al—S—O Material 4[5] | 2 | 84.0 | 11.9 | 1.9 | 2.2 | 16.0 |
| AlCl₃ + Al—S—O Material 5[6] | 2 | 92.3 | 5.0 | 1.3 | 1.4 | 7.7 |

[1] prepared from Solution 6 without (NH₄)₂SO₄; S:Al atomic ratio: 0
[2] prepared from Solution 1, S:Al atomic ratio: 0.1:1
[3] prepared from Solution 2, S:Al atomic ratio: 0.25:1
[4] prepared from Solution 3, S:Al atomic ratio: 0.5:1
[5] prepared from Solution 4, S:Al atomic ratio: 1.0:1
[6] prepared from Solution 5, S:Al atomic ratio: 0.5:1

TABLE II

| | | (Feed: Isopentane) | | | | |
|---|---|---|---|---|---|---|
| | Reaction | Liquid Product Composition (Weight-%) | | | | % Conversion |
| Catalyst Preparation Method | Time (Hours) | Isopentane | n-Pentane | C₄⁻ Alkanes | C₆⁺ Alkanes | of Isopentane |
| AlCl₃ + Alumina (Control)* | 1 | 98.0 | 1.0 | 0.3 | 0.7 | 2.0 |
| AlCl₃ + Al—S—O Material 1* | 1 | 94.2 | 2.0 | 0.7 | 3.1 | 5.8 |
| AlCl₃ + Al—S—O Material 2* | 1 | 88.4 | 5.8 | 2.2 | 3.6 | 11.6 |
| AlCl₃ + Al—S—O Material 3* | 1 | 88.6 | 6.1 | 1.0 | 4.3 | 11.4 |
| AlCl₃ + Al—S—O Material 4* | 1 | 95.5 | 1.2 | 1.0 | 2.3 | 4.5 |
| AlCl₃ + Al—S—O Material 5* | 1 | 97.1 | 1.2 | 0.7 | 1.0 | 2.9 |
| AlCl₃ + Alumina (Control)* | 2 | 97.1 | 1.4 | 0.8 | 0.7 | 2.9 |
| AlCl₃ + Al—S—O Material 1* | 2 | 92.8 | 2.7 | 2.0 | 2.6 | 7.2 |
| AlCl₃ + Al—S—O Material 2* | 2 | 73.5 | 8.9 | 7.0 | 10.7 | 26.5 |
| AlCl₃ + Al—S—O Material 3* | 2 | 71.2 | 10.2 | 2.9 | 15.7 | 28.8 |
| AlCl₃ + Al—S—O Material 4* | 2 | 92.5 | 2.0 | 2.4 | 3.1 | 7.5 |
| AlCl₃ + Al—S—O Material 5* | 2 | 94.8 | 2.3 | 1.1 | 1.8 | 5.2 |

*See footnotes in Table I

TABLE III

| Catalyst Preparation Method | Reaction Time (Hours) | (Feed: n-Hexane) Liquid Product Composition (Weight-%) | | | | % Conversion of n-Hexane |
|---|---|---|---|---|---|---|
| | | n-Hexane | Isohexanes[1] | $C_4$–$C_5$ Alkanes | $C_7^+$ Alkanes | |
| $AlCl_3$ + Alumina (Control)* | 1 | 99.1 | 0.6 | 0.2 | 0.1 | 0.9 |
| $AlCl_3$ + Al—S—O Material 1* | 1 | 94.8 | 3.4 | 0.4 | 1.4 | 5.2 |
| $AlCl_3$ + Al—S—O Material 2* | 1 | 92.8 | 5.6 | 1.0 | 0.5 | 7.2 |
| $AlCl_3$ + Al—S—O Material 3* | 1 | 85.7 | 11.7 | 1.4 | 1.3 | 14.3 |
| $AlCl_3$ + Al—S—O Material 4* | 1 | 97.9 | 1.4 | 0.4 | 0.3 | 2.1 |
| $AlCl_3$ + Al—S—O Material 5* | 1 | 98.6 | 0.8 | 0.3 | 0.3 | 1.4 |
| $AlCl_3$ + Alumina (Control)* | 2 | 92.2 | 1.0 | 0.5 | 0.3 | 1.8 |
| $AlCl_3$ + Al—S—O Material 1* | 2 | 94.8 | 4.1 | 0.6 | 0.5 | 5.2 |
| $AlCl_3$ + Al—S—O Material 2* | 2 | 91.3 | 6.7 | 1.2 | 0.8 | 8.7 |
| $AlCl_3$ + Al—S—O Material 3* | 2 | 83.7 | 12.6 | 2.0 | 1.7 | 16.3 |
| $AlCl_3$ + Al—S—O Material 4* | 2 | 97.4 | 1.8 | 0.4 | 0.4 | 2.6 |
| $AlCl_3$ + Al—S—O Material 5* | 2 | 98.3 | 1.0 | 0.3 | 0.3 | 1.7 |

*See footnotes in Table I
[1] mainly methylpentane, some dimethylbutane

TABLE IV

| Catalyst Preparation | Reaction Time (Hours) | (Feed: Methylcyclopentane) Liquid Product Composition (Weight-%) | | % Conversion Methylcyclopentane |
|---|---|---|---|---|
| | | Methylcyclopentane | Cyclohexane | |
| $AlCl_3$ + Alumina (Control)* | 1 | 93.4 | 6.5 | 6.7 |
| $AlCl_3$ + Al—S—O Material 1* | 1 | 88.1 | 11.6 | 11.9 |
| $AlCl_3$ + Al—S—O Material 2* | 1 | 81.3 | 18.2 | 18.7 |
| $AlCl_3$ + Al—S—O Material 3* | 1 | 59.3 | 40.0 | 40.7 |
| $AlCl_3$ + Al—S—O Material 4* | 1 | 85.4 | 14.2 | 14.6 |
| $AlCl_3$ + Al—S—O Material 5* | 1 | 89.6 | 10.1 | 10.4 |
| $AlCl_3$ + Alumina (Control)* | 2 | 91.3 | 8.6 | 8.7 |
| $AlCl_3$ + Al—S—O Material 1* | 2 | 81.5 | 17.9 | 18.5 |
| $AlCl_3$ + Al—S—O Material 2* | 2 | 70.9 | 28.3 | 29.1 |
| $AlCl_3$ + Al—S—O Material 3* | 2 | 38.5 | 60.5 | 61.5 |
| $AlCl_3$ + Al—S—O Material 4* | 2 | 82.3 | 17.1 | 17.7 |
| $AlCl_3$ + Al—S—O Material 5* | 2 | 88.2 | 11.5 | 11.8 |

*See footnotes in Table I

Test data in Tables I–IV clearly show that the catalysts prepared from $AlCl_3$ and Al-S-O Materials 1–4 were consistently more active for alkane and cycloalkane isomerization (as evidenced by higher hydrocarbon feed conversion) than a control catalyst which did not contain aluminum sulfate and a catalyst prepared from $AlCl_3$ and A-S-O Material 5 (S:Al atomic ratio 1.5:1). The most effective (and thus more preferred) catalysts were Catalyst Materials 2 and 3 prepared from solutions having S:Al atomic ratios (i.e., $SO_4$:Al molar ratios) of about 0.25 to about 0.5:1.

EXAMPLE III

This example illustrate the preparation of composition from $AlCl_3$ and inorganic support materials in the presence of various sulfur-containing acids, and the use of these compositions as catalysts for isomerizing methylcyclopentane to cyclohexane.

The catalysts according to the second embodiment of this invention were prepared by mixing 1.78 g (13.3 millimoles) $AlCl_3$, various amounts of one of four sulfur-containing acids (fuming sulfuric acid containing about 30 weight-% free $SO_3$, dry chlorosulfonic acid, dry fluorosulfonic acid and dry trifluoromethanesulfonic acid), 2.50 g of one of three inorganic support materials (described below) which had been calcined at 600° C. for 2 hours, and 35 mL of freshly distilled $CCl_4$; heating the obtained mixture overnight (for about 16 hours) under reflux conditions in a dry nitrogen atmosphere; and evaporating the solvent from the finished reaction mixture under vacuum conditions (0.1 mm Hg) for several hours so as to obtain dry catalyst compositions. The acids were employed in such quantities as to attain molar ratios of acid to $AlCl_3$ in the range of 0.1:1 to about 2.0:1 (as indicated in Table V). The following solid inorganic support materials were employed: gamma-alumina (100 mesh trilobal extrudate, marketed by American Cyanamid Company, Deerfield, Ill., having a BET/$N_2$ surface area of 180 m²/g), silica (marketed by the Davison Catalyst Division of W. R. Grace and Company, Baltimore, Md., under the product designation of G-57, having a BET/$N_2$ surface area of 340 m²/g), and silica/alumina (containing 25 weight-% $SiO_2$ and 75 weight-% $Al_2O_3$, having a BET/$N_2$ surface area of about 300 m²/g, and having been prepared by coprecipitating hydrated silica and hydrated alumina, followed by drying and calcining of the coprecipitate). Corresponding control catalysts were prepared substantially in the same manner as the invention catalysts, except that no sulfur-containing acid was present.

The above-described catalyst compositions were employed in the isomerization of methylcyclopentane to cyclohexane at essentially the same reaction conditions as those described in Example II. Test results which were obtained after a 1 hour reaction time (essentially in accordance with the method described in Example II) are summarized in Table V.

TABLE V

| Catalyst Preparation Method | | | Acid:$AlCl_3$ Molar Ratio | % Conversion of Methylcyclopentane |
|---|---|---|---|---|
| Al Halide | Support Material | Acid | | |
| $AlCl_3$ | $Al_2O_3$ | None | 0 | 3.2 |

TABLE V-continued

| Catalyst Preparation Method | | | Acid:AlCl₃ | % Conversion |
|---|---|---|---|---|
| Al Halide | Support Material | Acid | Molar Ratio | of Methylcyclopentane |
| " | " | H₂SO₄ | 0.19:1 | 8.8 |
| " | " | " | 0.38:1 | 13.1 |
| " | " | " | 0.56:1 | 16.0 |
| " | " | " | 0.75:1 | 38.8 |
| " | " | ClSO₃H | 0.19:1 | 28.6 |
| " | " | " | 0.38:1 | 34.4 |
| " | " | " | 0.56:1 | 64.4 |
| " | " | " | 0.75:1 | 49.7 |
| " | " | " | 1.00:1 | 26.2 |
| " | " | " | 1.50:1 | 3.4 |
| " | " | " | 2.00:1 | 1.0 |
| " | " | FSO₃H | 0.19:1 | 7.5 |
| " | " | " | 0.38:1 | 7.0 |
| " | " | " | 0.56:1 | 11.7 |
| " | " | " | 0.75:1 | 27.7 |
| " | " | CF₃SO₃H | 0.38:1 | 7.9 |
| " | " | " | 0.56:1 | 3.6 |
| " | " | " | 0.75:1 | 7.5 |
| " | " | " | 1.00:1 | 7.5 |
| " | SiO₂ | None | 0 | 2.7 |
| " | " | H₂SO₄ | 0.19:1 | 20.7 |
| " | " | " | 0.38:1 | 47.8 |
| " | " | " | 0.56:1 | 39.0 |
| " | " | " | 0.75:1 | 31.3 |
| " | " | ClSO₃H | 0.19:1 | 17.6 |
| " | " | " | 0.38:1 | 37.8 |
| " | " | " | 0.56:1 | 49.8 |
| " | " | " | 0.75:1 | 42.6 |
| " | " | " | 1.00:1 | 16.0 |
| " | " | " | 1.50:1 | 4.5 |
| " | " | " | 2.00:1 | 0.7 |
| " | " | FSO₃H | 0.19:1 | 11.4 |
| " | " | " | 0.38:1 | 13.1 |
| " | " | " | 0.56:1 | 19.3 |
| " | " | " | 0.75:1 | 24.8 |
| " | " | " | 1.00:1 | 2.9 |
| " | " | " | 1.50:1 | 0.6 |
| " | " | CF₃SO₃H | 0.38:1 | 7.8 |
| " | " | " | 0.56:1 | 7.4 |
| " | " | " | 0.75:1 | 6.9 |
| " | " | " | 1.00:1 | 5.9 |
| AlCl₄ | SiO₂—Al₂O₃ | None | 0 | 2.5 |
| " | " | " | " | 1.9 |
| " | " | ClSO₃H | 0.19:1 | 18.0 |
| " | " | " | 0.38:1 | 62.7 |
| " | " | " | 0.56:1 | 47.0 |
| " | " | " | 0.75:1 | 78.7 |
| " | " | " | 1.00:1 | 29.8 |
| " | " | " | 1.50:1 | 5.2 |
| " | " | " | 2.00:1 | 3.1 |
| " | " | FSO₃H | 0.19:1 | 14.0 |
| " | " | " | 0.38:1 | 20.9 |
| " | " | " | 0.56:1 | 19.9 |
| " | " | " | 0.75:1 | 18.7 |

Note:
The formed isomerization products in all tests consisted essentially of cyclohexane.

Test results in Table V clearly show that the catalysts prepared in the presence of one of the sulfur-containing acids at an acid:AlCl₃ molar ratio of about 0.19:1 to about 1:1 were consistently more active as methylcyclopentane isomerization catalysts than those prepared in the absence of one of these acids. The catalyst materials having been prepared at an acid:AlCl₃ molar ratio of about 0.38:1 to about 0.75:1 were particularly active and are presently more preferred.

The above-described catalyst compositions were also employed as catalysts in the isomerization/disproportionation of n-pentane, isopentane and n-hexane, respectively, essentially at the same reaction conditions as those described in Example II. Preliminary test results indicate that the catalyst compositions having been prepared from AlCl₃, one of the above-described sulfur-containing acids and a support material (Al₂O₃ or SiO₂ or SiO₂-Al₂O₃), at acid:AlCl₃ molar ratios of about 0.19:1 to about 1:1 were frequently (but not always) more active alkane isomerization/disproportionation catalysts than the corresponding catalyst materials which had been prepared without a sulfur-containing acid.

Reasonable variations, modifications and adaptations for various conditions and reactants can be made within the scope of the disclosure and the appended claims without departing from the scope of this invention.

That which is claimed is:

1. A process for isomerizing saturated hydrocarbons which comprises contacting, at a reaction temperature of about 0°–100° C., at least one saturated hydrocarbon selected from the group consisting of alkanes containing 4–10 carbon atoms per molecule and cycloalkanes containing 5–10 carbon atoms per molecule with a solid catalyst composition at effective isomerization conditions;

wherein said catalyst composition has been prepared by a method comprising the steps of (I) heating in the substantial absence of water, at a temperature of about 40°-90° C., a mixture comprising (a) aluminum chloride, (b) at least one chlorinated hydrocarbon selected from the group consisting of dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane, and (c) at least one solid aluminum sulfate-containing support material having been prepared by a method which comprise (1) combining an aqueous solution of at least one aluminum salt with an aqueous solution of ammonium sulfate such as to provide a $SO_4$:Al molar ratio of about 0.1:1 to about 1:1 in the obtained combined solution, (2) adding an aqueous alkaline solution of at least one base selected from the group consisting of NaOH, KOH and $NH_3$ to the combined aqueous solution of the aluminum salt and ammonium sulfate obtained in step (1) so as to raise the pH of said combined aqueous solution to at least about 8 and to form a precipitate, (3) separating the precipitate formed in step (2) from the combined aqueous solution, and (4) calcining the separated precipitate formed in step (3) at about 500°-700° C. for at least about 1 hour; and (II) separating the solid material contained in the reaction mixture obtained in step (I) from said at least one chlorinated hydrocarbon under a dry gas atmosphere.

2. A process in accordance with claim 1, wherein said at least one chlorinated hydrocarbon is carbon tetrachloride.

3. A process in accordance with claim 1, wherein the weight ratio of agent (a) to agent (c) is about 0.6:1 to about 0.8:1.

4. A process in accordance with claim 1, wherein said at least one aluminum salt is aluminum nitrate and said at least one base is ammonium hydroxide.

5. A process in accordance with claim 1, wherein said $SO_4$:Al molar ratio is about 0.25:1 to about 0.5:1.

6. A process in accordance with claim 1, wherein the pH of the combined solution obtained in preparation step (2) is about 9-12.

7. A process in accordance with claim 1, wherein said effective isomerization conditions comprise a reaction temperature of about 20°-50° C. and a reaction time of about 0.1-8 hours.

8. A process in accordance with claim 1, wherein said at least one saturated hydrocarbon is at least one alkane containing 4-10 carbon atoms per molecule.

9. A process in accordance with claim 8, wherein said at least one alkane is selected from the group consisting of n-pentane, isopentane and n-hexane.

10. A process in accordance with claim 1, wherein said at least one saturated hydrocarbon is at least one cycloalkane containing 5-10 carbon atoms per molecule.

11. A process in accordance with claim 10, wherein said at least one cycloalkane is methylcyclopentane.

12. A process for isomerizing saturated hydrocarbons which comprises contacting, at a temperature of about 0°-100° C., at least one saturated hydrocarbon selected from the group consisting of cycloalkanes containing 5-10 carbon atoms per molecule with a solid catalyst composition at effective isomerization conditions;

wherein said solid catalyst composition has been prepared by a method comprising the steps of (A) heating in the substantial absence of water, at a temperature of about 40°-90° C., a mixture comprising (i) aluminum chloride, (ii) at least one sulfur-containing acid selected from the group consisting of sulfuric acid, chlorosulfonic acid, fluorosulfonic acid and trifluoromethanesulfonic acid, (iii) at least one inorganic support having a surface area of at least about 50 $m^2/g$ selected from the group consisting of alumina, silica and silica-alumina, and (iv) at least one chlorinated hydrocarbon selected from the group consisting of dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane, wherein the molar ratio of agent (ii) to agent (i) is in the range of about 0.1:1 to about 1:1; and (B) separating the solid material contained in the reaction mixture obtained in step (A) from said at least one chlorinated hydrocarbon under a dry gas atmosphere.

13. A process in accordance with claim 12, wherein said at least one chlorinated hydrocarbon is carbon tetrachloride.

14. A process in accordance with claim 12, wherein said at least one sulfur-containing acid is sulfuric acid.

15. A process in accordance with claim 12, wherein said at least one sulfur-containing acid is selected from the group consisting of chlorosulfonic acid, fluorosulfonic acid and trifluoromethanesulfonic acid.

16. A process in accordance with claim 12, wherein the surface area of said at least one inorganic support material is about 100-400 $m^2/g$.

17. A process in accordance with claim 12, wherein the molar ratio of agent (ii) to agent (i) is about 0.19:1 to about 1:1.

18. A process in accordance with claim 17, wherein the weight ratio of agent (i) to agent (iii) is about 0.6:1 to about 0.8:1.

19. A process in accordance with claim 12, wherein said effective isomerization conditions comprise a reaction temperature of about 20°-50° C. and a reaction time of about 0.1-8 hours.

20. A process in accordance with claim 12, wherein said at least one saturated hydrocarbon is methylcyclopentane.

* * * * *